(12) United States Patent
Bille

(10) Patent No.: US 7,987,077 B2
(45) Date of Patent: Jul. 26, 2011

(54) SYSTEM AND METHOD FOR SIMULATING AN LIOB PROTOCOL TO ESTABLISH A TREATMENT PLAN FOR A PATIENT

(75) Inventor: Josef F. Bille, Heidelberg (DE)

(73) Assignee: Technolas Perfect Vision GmbH, Munich (DE)

( * ) Notice: Subject to any disclaimer, the term of this patent is extended or adjusted under 35 U.S.C. 154(b) by 424 days.

(21) Appl. No.: 12/029,314

(22) Filed: Feb. 11, 2008

(65) Prior Publication Data

US 2009/0187387 A1 Jul. 23, 2009

Related U.S. Application Data

(63) Continuation-in-part of application No. 12/016,857, filed on Jan. 18, 2008, now Pat. No. 7,844,425.

(51) Int. Cl.
*G06F 9/455* (2006.01)
(52) U.S. Cl. .......................................................... 703/6
(58) Field of Classification Search .................. 703/2, 6; 606/4, 5, 11; 351/205, 212; 702/66; 250/307; 607/89

See application file for complete search history.

(56) References Cited

U.S. PATENT DOCUMENTS

| | | | |
|---|---|---|---|
| 2004/0054358 A1 | 3/2004 | Cox et al. | |
| 2004/0243112 A1* | 12/2004 | Bendett et al. | 606/5 |
| 2005/0251115 A1* | 11/2005 | Cox et al. | 606/4 |
| 2007/0142826 A1 | 6/2007 | Sacharoff | |
| 2007/0161972 A1* | 7/2007 | Felberg et al. | 606/4 |
| 2008/0015662 A1* | 1/2008 | Tunnermann et al. | 607/89 |
| 2008/0051769 A1* | 2/2008 | Mrochen et al. | 606/4 |
| 2008/0051772 A1* | 2/2008 | Suckewer et al. | 606/5 |
| 2008/0073525 A1* | 3/2008 | Gross et al. | 250/307 |
| 2008/0100803 A1* | 5/2008 | Dick et al. | 351/212 |
| 2008/0140329 A1* | 6/2008 | Dai | 702/66 |
| 2008/0252848 A1* | 10/2008 | Dai | 351/205 |
| 2008/0287935 A1* | 11/2008 | Bille | 606/11 |
| 2009/0005764 A1* | 1/2009 | Knox et al. | 606/5 |
| 2009/0118718 A1* | 5/2009 | Raksi et al. | 606/5 |
| 2009/0157061 A1* | 6/2009 | Ruiz et al. | 606/5 |
| 2009/0157063 A1* | 6/2009 | Ruiz et al. | 606/5 |
| 2009/0187171 A1* | 7/2009 | Loesel et al. | 606/5 |
| 2009/0187386 A1* | 7/2009 | Bille et al. | 703/2 |
| 2009/0264873 A1* | 10/2009 | Loesel et al. | 606/5 |
| 2010/0130967 A1* | 5/2010 | Glasmacher et al. | 606/5 |

OTHER PUBLICATIONS

Breitenfeld et al., "Finite element method simulation of the human lens during accommodation", 2005.*

(Continued)

*Primary Examiner* — Kandasamy Thangavelu
(74) *Attorney, Agent, or Firm* — Nydegger & Associates

(57) ABSTRACT

A system and method are provided for simulating a Laser Induced Optical Breakdown (LIOB) protocol to establish a surgical LIOB treatment for a patient. In the system, a library of finite element models characterizing various visual defects in corneas are programmed into a computer. Further, a library of nomograms indicating specific LIOB protocols for correcting respective visual defects are programmed into the computer. As a result, a model and a corresponding nomogram may be selected in view of a patient's diagnostic information. Further, the selected model may be individualized with the diagnostic information to more precisely characterize the patient's visual defects. Thereafter, the computer simulates the indicated LIOB protocol on the individualized model in order to achieve a desired corneal configuration. When the desired corneal configuration is achieved, the final treatment plan may be determined.

17 Claims, 3 Drawing Sheets

OTHER PUBLICATIONS

Juhasz et al., "Corneal Refractive surgery with Femtosecond lasers", IEEE 1999.*

Zohdy et al., "Acoustic estimation of thermal distribution in the vicinity of femtosecond laser induced optical breakdown", IEEE 2006.*

Zohdy et al., "An ultrasonic method to measure effective temperature in the vicinity of laser induced optical breakdown", IEEE 2003.*

Wirbelauer et al., "Experimental evaluation of online optical coherence pachymetry for corneal refractive surgery", 2003.*

Ruiz, L. A., MD. "Preliminary clinical results of non-invasive, intrastromal correction of presbyopia using the FEMTEC femtosecond laser system", Hawaiian Eye Meeting (2008).

Anderson, K., El-Sheikh, A., & Newson, T., "Application of structural analysis to the mechanical behaviour of the cornea", The Royal Society, (2004).

Anderson, K., El-Sheikh, A., & Newson, T., "FEA of the biomechanics of procine corneas", The Structural Engineer, (2004).

Crouch, Jessica R., Merriam, John C., and Crouch, Earl R. "Finite Element Model of Cornea Deformation." Medical Image Computing and Computer-Assisted Intervention. Springer Berlin. Heidelberg, Germany, 2005. 591-598.

Scherer, K.,P., Eggert, H., Guth, H., Stiller, P., "Biomechanical simulations for refractive corneal eye surgery", Proceedings of the IASTED International Conference, (2001).

Jouve, Francois and Hanna, Khalil, "Computer Simulations of Refractive Surgery and Accomodation Mechanisms", IUTAM Symposium on Synthesis in Bio Solid Mechanics. Springer Netherlands, (2006).

Zhang, Hongwei, "Finite Element Modeling of the Cornea and its Application in the Refractive Surgery", A Study of Aberrations in the Human Eye by Zernike Phase Plate Precompensation and Finite Element Modeling Methods, Chapter 1, pp. 1-26, 2007, Heilongjiang, China.

* cited by examiner

US 7,987,077 B2

SYSTEM AND METHOD FOR SIMULATING AN LIOB PROTOCOL TO ESTABLISH A TREATMENT PLAN FOR A PATIENT

This application is a continuation-in-part of application Ser. No. 12/016,857, filed Jan. 18, 2008, now U.S. Pat. No. 7,844,425. The contents of application Ser. No. 12/016,857 are incorporated herein by reference.

FIELD OF THE INVENTION

The present invention pertains generally to computer simulations. More particularly, the present invention pertains to computer simulations that use a finite element model to predict the reshaping of a cornea in response to Laser Induced Optical Breakdown (LIOB). The present invention is particularly, but not exclusively useful as a system or method for modifying a corneal configuration defined by a finite element model with an LIOB protocol indicated by a nomogram to determine a final LIOB treatment plan for correcting a visual defect.

BACKGROUND OF THE INVENTION

Basically, refractive surgery involves a reshaping of the cornea to correct for optical aberrations. Although such reshaping can be accomplished in several ways, for purposes of the present invention it is envisioned that refractive surgery will be accomplished in accordance with protocols disclosed in the co-pending application for an invention entitled "Method for Intrastromal Refractive Surgery," which is assigned to the same assignee as the present invention. The contents of this co-pending application are incorporated herein by reference.

In any surgical procedure, a preliminary diagnostic evaluation of the patient is essential. Moreover, for extremely complicated surgeries such as ophthalmic laser surgery, an accurate evaluation is essential for determining how the surgery should be accomplished. Further, and particularly with ophthalmic surgery, an evaluation helps determine the scope and extent of the surgery that is required. With so many variables involved, however, the ability to predict a surgical outcome with a high level of assurance can be extremely helpful.

As disclosed in the parent application, from which the present invention is a continuation, the use of a finite element model can be very helpful for predicting the outcome of an ophthalmic laser surgery procedure. Specifically, the finite element model disclosed in this parent application simulates a cornea and its response to a predetermined protocol for Laser Induced Optical Breakdown (LIOB) of stromal tissue in the cornea.

Every eye is unique and, accordingly, each eye has its own particular anatomical characteristics. Nevertheless, it happens that patients having similar vision defects will also have many similar anatomical characteristics in their respective corneas. Thus, in general, a finite element model may represent a corneal structure that exhibits a particular visual defect. Individualizing the model for a particular patient is then primarily a matter of scaling.

Further, a history of surgical treatments for a particular visual defect may produce a nomogram that indicates a particular LIOB protocol. Specifically, after performing LIOB on patients having essentially the same visual defect, the LIOB protocols and results may be analyzed and compiled to create a nomogram for future surgeries. The LIOB protocol indicated by this nomogram can be applied with a high degree of reliability for patients outside the group who have the same vision defect. This will be so, even though exact measures of corresponding values may be unknown. The consequence here is that a diagnostic nomogram which is characteristic of a surgical correction for a particular vision defect can be representative of a successful LIOB procedure for each member in an extended group of patients.

Zernike polynomials that mathematically model corneas having visual defects are given in the general form as:

$$W(\rho,\theta) = \Sigma c_{nm} Z_{nm}(\rho,\theta,\alpha_{nm})$$

In the above expression, "n" pertains to the order of the polynomial (i.e. $2^{nd}$ or $3^{rd}$ order aberration) and "m" pertains to frequency (i.e. $\theta$, $2\theta$, and $3\theta$). Further, $c_{nm}$ is a coefficient that pertains to magnitude; and $Z_{nm}(\rho,\theta,\alpha_{nm})$ depends on radial and azimuthal considerations as they relate to a particular axis ($\alpha_{nm}$).

When considering the human eye as a genuine optical system, aberrations can be generally categorized as being either symmetric or asymmetric with respect to the optical axis of the eye. For this categorization, symmetrical aberrations are radially symmetrical with respect to the optical axis, while the asymmetrical aberrations are not. As indicated by the Zernike polynomials, in addition to their symmetry or lack thereof, the various optical aberrations of the eye can be categorized by their order. Insofar as imaging is concerned, it happens that the so-called lower order aberrations (i.e. $2^{nd}$, $3^{rd}$ and $4^{th}$ order) can be significantly detrimental. These lower order aberrations include both symmetrical and asymmetrical aberrations.

For purposes of the present invention, an appreciation for the interactive use of a particular model with Zernike polynomials for a finite element model is important. Specifically, it is known that a model can be created which will be representative of the cornea in all patients exhibiting a substantially same vision defect (e.g. presbyopia). Further, it is known that Zernike polynomials can be used to create the model. Using specific measurement values from a particular cornea, the Zernike polynomials can then be scaled to mathematically represent the optical condition of the particular cornea. Importantly, a model having this mathematical representation can then be used with a nomogram in a subsequent LIOB simulation. Further, the continuing modification of the model through LIOB simulation can lead to a desired corneal configuration. As a result, the necessary LIOB protocol to achieve the desired corneal configuration may be identified.

In light of the above, it is an object of the present invention to create a system and method for simulating a Laser Induced Optical Breakdown (LIOB) protocol to establish a surgical LIOB treatment for a patient. Another object of the present invention is provide a library of various nomograms and associated finite element models corresponding to respective visual defects for selected use in simulating LIOB procedures. Still another object of the present invention is to provide a system and method for simulating an LIOB procedure that is simple to use, easy to implement and cost effective.

SUMMARY OF THE INVENTION

In accordance with the present invention, a system and method are provided for establishing a Laser Induced Optical Breakdown (LIOB) treatment plan for a patient. Specifically, it is envisioned that the system and method will utilize a library that includes a plurality of finite element models and a plurality of nomograms. For optimal performance, the library is installed on a computer to provide for a quick determination of the final treatment plan.

In the system, each finite element model in the library will characterize a cornea that exhibits a particular vision defect. Typically, the finite element models utilize Zernike polynomials, although other orthogonal polynomials or statistical models may be used. Specifically, a patient's corneal configuration may be mathematically represented by Zernike polynomials. More particularly, selected Zernike polynomials can be used with selected corneal configurations. For instance: myopia ($Z_4$); hyperopia ($Z_4$); presbyopia ($Z_4$); astigmatism ($Z_3$ and $Z_5$: $2^{nd}$ order); coma ($Z_7$ and $Z_8$: $3^{rd}$ order); trefoil ($Z_6$ and $Z_9$: $3^{rd}$ order) and spherical aberrations ($Z_{12}$: $4^{th}$ order). It will be appreciated by the skilled artisan that other mathematical representations can be used for this same purpose (e.g. Taylor polynomials or Fourier functions). Also, the present invention envisions the possibility that models other than a finite element model may be used. For instance, a multi-layered, thin shell model, or a model employing analytical estimations of viscoelastic changes may be used. Preferably, however, the present invention envisions a finite element model using Zernike polynomials.

For purposes of the present invention, the finite element model is preferably of a type disclosed and claimed in the parent application of the present invention. Essentially, the finite element model has a first plurality of elements for simulating biomechanical characteristics for a Bowman's capsule of a cornea. And, it also has a second plurality of elements for simulating biomechanical characteristics for a stroma of the cornea. As envisioned for the present invention, these various elements will be programmed to replicate the patient's corneal configuration.

For the system, each nomogram in the library will specify an LIOB treatment protocol for a particular visual defect. For instance, the library will include separate nomograms for respectively correcting myopia, hyperopia, presbyopia, astigmatism, coma, trefoil, or various common combinations of such visual defects. Typically, each nomogram is compiled by the collection of diagnostic information and surgical plans from many patients (e.g. more than one hundred patients). Specifically, this information is taken from patients having the substantially same vision defect. For example, conditions such as myopia, hyperopia, presbyopia, astigmatism, coma, trefoil, and spherical aberrations will each have a different nomogram. Most importantly, each nomogram is considered representative of a treatment for a corneal configuration for all patients with the particular vision defect. With time, each nomogram can be continuously updated by the subsequent inclusion of additional similar information.

From the above, it may be understood that each nomogram is associated with a particular visual defect, and each visual defect is associated with a specific corneal configuration. As a result, each model characterizing a particular corneal configuration will correspond to a particular nomogram. Therefore, for Zernike polynomial-based models, both the model and the corresponding nomogram are associated with a same Zernike polynomial.

In operation, the patient is initially evaluated to identify the visual defect(s) present in the patient's eye. Further, specific diagnostic information, such as the tensors at predetermined locations in the patient's cornea, are measured. After the patient is evaluated, a final desired corneal configuration resulting from surgery is determined. Further, a nomogram is selected to obtain the desired corneal configuration. Specifically, the selected nomogram will indicate an LIOB treatment protocol for correcting the visual defect noted by the patient evaluation. Also, a finite element model will be selected in conjunction with the nomogram. Mathematically, the finite element model will establish an initial corneal configuration that characterizes the patient's cornea. In order to more precisely model the patient's cornea, the diagnostic information obtained during patient evaluation may be input into the selected model. As a result, the model will define an individualized corneal configuration that more accurately represents the patient's cornea.

For the LIOB simulation, the computer has an electronic means for modifying the individualized corneal configuration. Specifically, the individualized corneal configuration is modified in accordance with the LIOB treatment protocol indicated by the selected nomogram. This modification is done to simulate the reshaping of a cornea in response to the indicated LIOB protocol. The computer also includes a means for determining the modified corneal configuration from the finite element model, after simulation of the LIOB protocol has been completed. The computer can then compare the modified corneal configuration with the desired corneal configuration to identify any difference therebetween that may serve as an error signal. If an error signal is present, the LIOB protocol can be appropriately modified in a fractionated process, and a subsequent simulation can be performed. If it is determined that further reduction in the error signal is not attainable, the computer can choose a new finite element model to characterize the modified corneal configuration. Thereafter, further simulation may be performed until the desired corneal configuration is obtained.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
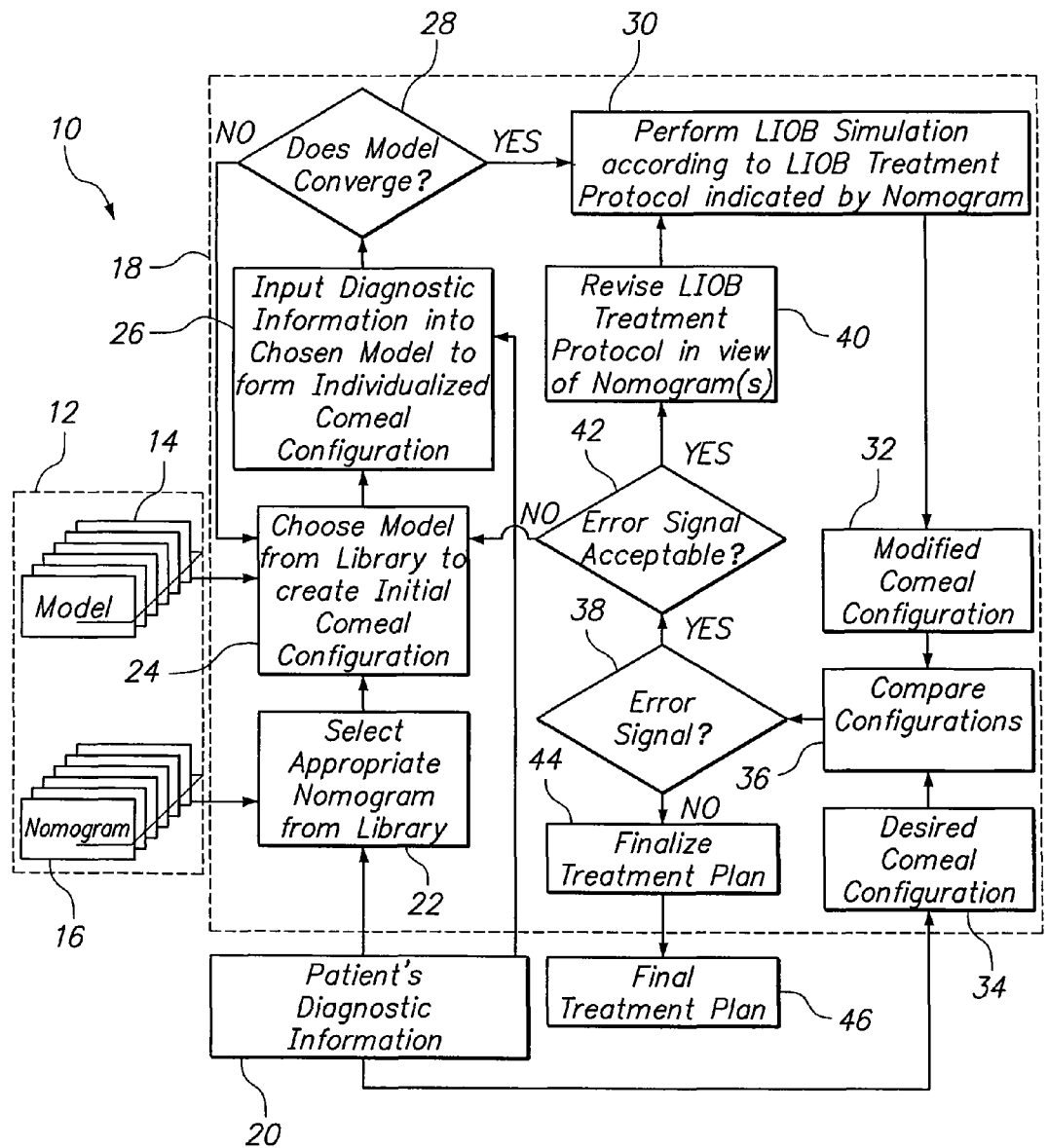
FIG. 1 is a schematic view of a system for determining a treatment plan for ophthalmic surgery in accordance with the present invention.

Referring initially to FIG. 1, a system for determining a final treatment plan for ophthalmic surgery is shown and generally designated 10. As shown in FIG. 1, the system 10 includes a library 12 that stores a plurality of finite element models 14 and a plurality of nomograms 16. For the system 10, the library 12 may be installed or temporarily input into a computer 18.

Mathematically, the models 14 approximate shapes and fractions of shapes that correspond to the structure of a cornea. For purposes of the present invention, the models 14 may use Zernike polynomials, other orthogonal polynomials, or functions resulting from statistical analysis. For each finite element model 14, a unique number of elements observed in a cornea may be required. Further, each finite element model 14 may have a unique mathematical structure. As a result, any given cornea structure may be represented by a plurality of models 14 that provide varying accuracy in simulating the corneal structure. In any event, the models 14 may approximate aberrations in a cornea.

In the system 10, each nomogram 16 indicates an LIOB protocol that is used in ophthalmic surgery to correct a particular visual defect, or a particular group of visual defects. Typically, a nomogram 16 is created after analyzing the results of multiple surgical treatments of an optical condition found in successive patients. For instance, a surgeon may perform ophthalmic surgery on one hundred patients who exhibit a similar optical aberration like astigmatism. Upon analyzing the treatment plans and surgical results for these one hundred patients, the surgeon creates a nomogram 16. An exemplary nomogram 16 may require a cylindrical cut in the cornea at a specified distance from the optical axis. This nomogram 16 may then be followed during surgery on subsequent patients exhibiting a similar visual defect.

Because each specific nomogram 16 is associated with a specific visual defect, each nomogram 16 is associated with the structure of a cornea exhibiting that defect. Further, as noted above, a plurality of models 14 approximate shapes and fractions of shapes corresponding to the structure of a specific cornea. Therefore, it may be understood that a specific nomogram 16 corresponds to a model 14 or a specific group of models 14 that may be used to simulate the cornea.

With this understanding of nomograms 16 and models 14, the method for determining an ophthalmic surgical treatment plan may be understood. As shown in FIG. 1, at action block 20, a patient is initially examined and diagnostic information about the patient's visual defects is obtained.

Specifically, the diagnostic information may include a diagnosis of a visual defect or defects. Further, the diagnostic information may include specified intracorneal biomechanical data, such as tensors, at certain locations in the cornea. As shown in block 22, a doctor or the computer 18 may select the appropriate nomogram 16 from the library 12 in view of the diagnostic information. Specifically, the selected nomogram 16 indicates an LIOB protocol previously used to correct visual defects similar to those exhibited by the patient.

As shown in FIG. 1, in conjunction with the selection of the nomograms 16, the computer 18 chooses a model 14 from the library 12 to create an initial corneal configuration representative of the patient's cornea (block 24). After the model 14 is chosen, the specific diagnostic information is entered into the chosen model 14 to individualize the model 14 and form an individualized corneal configuration (block 26). Once the chosen model 14 is individualized, the computer 18 determines whether the individualized model 14 can be used in an LIOB simulation. Specifically, the computer 18 must determine whether the individualized model 14 converges at inquiry block 28. If the individualized model 14 fails to converge, then the computer 18 chooses another model 14 at block 24, and individualizes it at block 26. After an individualized model 14 is found to converge at inquiry block 28, the computer 18 performs an LIOB simulation (action block 30). This simulation is performed according to the LIOB treatment protocol indicated by the nomogram 16 selected from the library 12 at block 22. As a result of the LIOB simulation, the computer 18 predicts the structural effect on the initial corneal configuration to establish a modified corneal configuration (action block 32).

As shown in FIG. 1, a desired corneal configuration is determined in view of the patient's diagnostic information and is stored in the computer 18 (at action block 34). In the method of the present invention, the computer 18 compares the desired corneal configuration with the modified corneal configuration at action block 36. As a result of the comparison at action block 36, the computer 18 determines whether there is an error signal. Specifically, the computer 18 determines whether there is a non-negligible difference between the desired corneal configuration and the modified corneal configuration (inquiry block 38).

In the initial iteration, or in subsequent iterations in which the error signal (the difference between the modified and final corneal configurations) is reduced, the method moves from inquiry block 38 to action block 40. At action block 40, the computer 18 revises the LIOB procedure. Specifically, the computer 18 revises the previously used nomogram 16 in view of the changes in the corneal configuration due to the previous LIOB simulation. For instance, the computer 18 may simply adjust the parameters of the currently used nomogram 16. Alternatively, the computer 18 may acquire another nomogram 16 from action block 22, and add a fractionated step or steps from the newly acquired nomogram 16 to the LIOB procedure. After the LIOB procedure is revised, the computer 18 again simulates LIOB at action block 30 to obtain a new modified corneal configuration (at action block 32). Thereafter, the configurations are compared at action block 36 to again determine the error signal.

Still referring to FIG. 1, it can be seen that the presence of an error signal at inquiry block 38 leads to inquiry block 42. At inquiry block 42, the computer 18 determines whether the error signal is acceptable, i.e., whether the error signal indicates that the LIOB protocol may be revised to further reduce the error signal. In this determination, the limits of the model 14 in use may be identified. Specifically, if the error signal is not reduced from a previous iteration, then the model 14 may not be suitable for continuing the characterization of the modified corneal configuration. Therefore, the inquiry block 42 provides for the computer 18 to select another model 14 at action block 24 to represent the modified corneal configuration. As may be understood, the method will then progress from action block 24 as previously indicated.

As shown at inquiry block 38, when the computer 18 finds no error signal, the method causes the finalization of a treatment plan at block 44. Specifically, the computer 18 compiles all successful procedures simulated at action block 34 to finalize the treatment plan. Further, the computer 18 optimizes the final treatment plan to eliminate redundant or unnecessary procedures during the compilation process. Thereafter, the final treatment plan is identified at action block 46.

Figure 2:
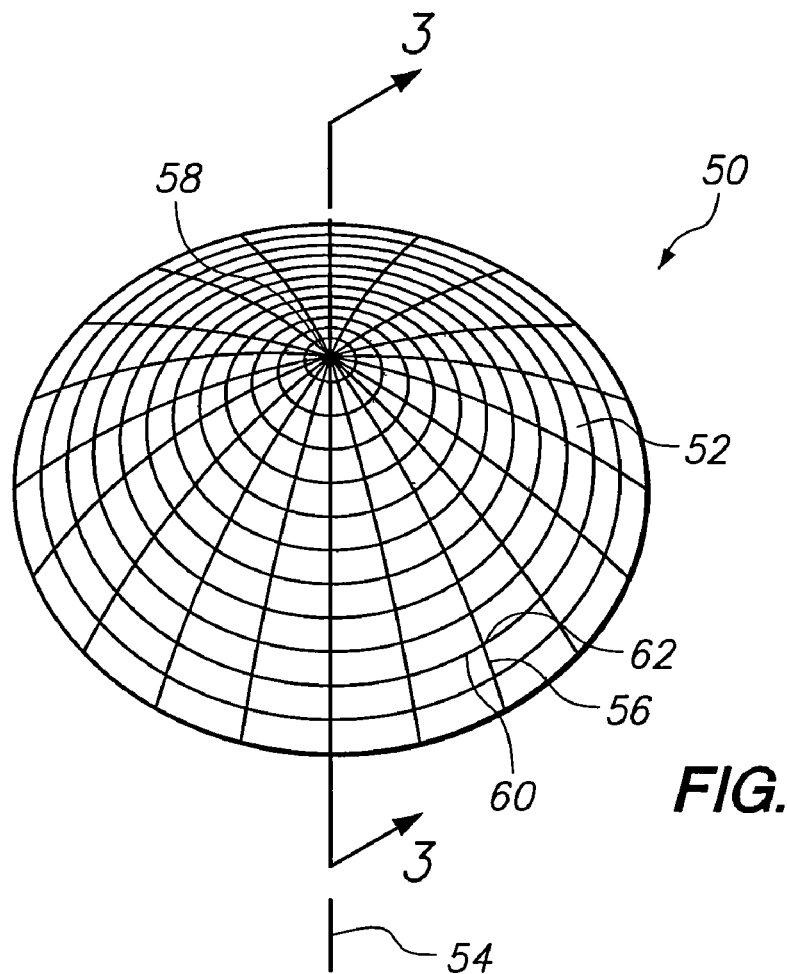
FIG. 2 is a perspective view of a layer of a finite element model in accordance with the present invention.
Figure 3:
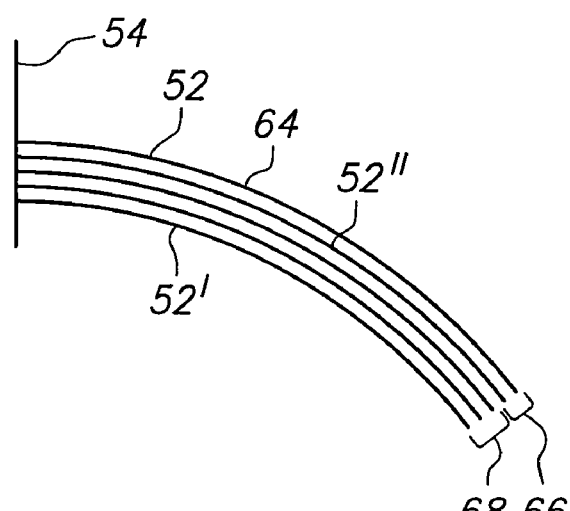
FIG. 3 is a cross-sectional view of a plurality of element lines, in a plurality of layers, in the finite element model as seen along the line 3-3 in FIG. 2.

Referring to FIGS. 2-3, a exemplary finite element model is discussed. In FIG. 2, a portion of a finite element model, generally designated 50, is shown in accordance with the present invention. The model 50 includes at least one layer 52, such as the one shown in FIG. 2. Preferably, however, it will include a plurality of layers 52, as more fully disclosed below. As will be appreciated with reference to FIG. 2, the model 50 defines an axis 54, and each layer 52 of the model 50 is, in part, defined by a plurality of lines 56 that radiate outwardly from the axis 54. Additionally, the layer 52 is shown with an apex 58, and the axis 54 is shown perpendicular to the layer 52 at the apex 58. Further, a plurality of rings 60 are centered on the axis 54, with each intersection of a line 56 with a ring 60 defining the location of an element 62. Thus, as shown, the finite element model 50 comprises a plurality of the elements 62.

FIG. 3 shows that the model 50 includes a plurality of different layers 52 (the layers 52' and 52" are only exemplary) in the simulated cornea 64. FIG. 3 also shows a first plurality 66 of layers 52 having a first group of elements 62 that are pre-programmed to simulate biomechanical characteristics for Bowman's Capsule in the simulated cornea 64. FIG. 3 also shows a second plurality 68 of layers 52 having a second group of elements 62 that are pre-programmed to simulate biomechanical characteristics in the stroma in the simulated cornea 64.

By way of example, the finite element model 50 preferably has nine layers 52. In these nine layers 52, the first (anterior) plurality 66 of layers 52 and elements 62 comprises three layers 52 that simulate Bowman's Capsule. The second (posterior) plurality 68 of layers 52 and elements 62 comprises six layers 52 and simulates stromal tissue in the simulated cornea 64. Additional layers 52 of elements 62, in each plurality 66 and 68, are, of course, possible.

Within the finite element model 50, each element 62 is three-dimensional. Mathematically, each element 62 is defined by tensors, with respective coefficients corresponding to bio-mechanical stresses and strains. In this case, coefficients for the pre-programmed elements of both the first and second groups are established according to diagnostic corneal data. Also, in line with anatomical consideration, the stress-scaling coefficient for Bowman's Capsule ($C_{Bowman}$) is approximately five times greater than the stress-scaling coefficient for the stroma ($C_{stroma}$).

In greater detail, the finite element model 50 for the present invention is axisymmetric and is based on a nonlinearly elastic, slightly compressible, transversely isotropic formulation with an isotropic exponential Lagrangian strain-energy function based on:

$$W = \tfrac{1}{2} C(e^Q - 1) + C_{compr}(I_3 \ln I_3 - I_3 + 1)$$

and $$Q = b_{ff} E^2_{ff} + b_{xx}(E^2_{cc} + E^2_{ss} + E^2_{cs} + E^2_{sc}) + b_{fx}(E^2_{fc} + E^2_{cf} + E^2_{fs} + E^2_{sf})$$

where:
I are invariants,
W is the strain potential (strain-energy function),
C is stress-scaling coefficient,
$C_{compr}$ is bulk modulus (kPa),
E is strain,
$b_{ff}$ is fiber strain exponent,
$b_{xx}$ is transverse strain component, and
$b_{fx}$ is fiber-transverse shear exponent.

Figure 4:
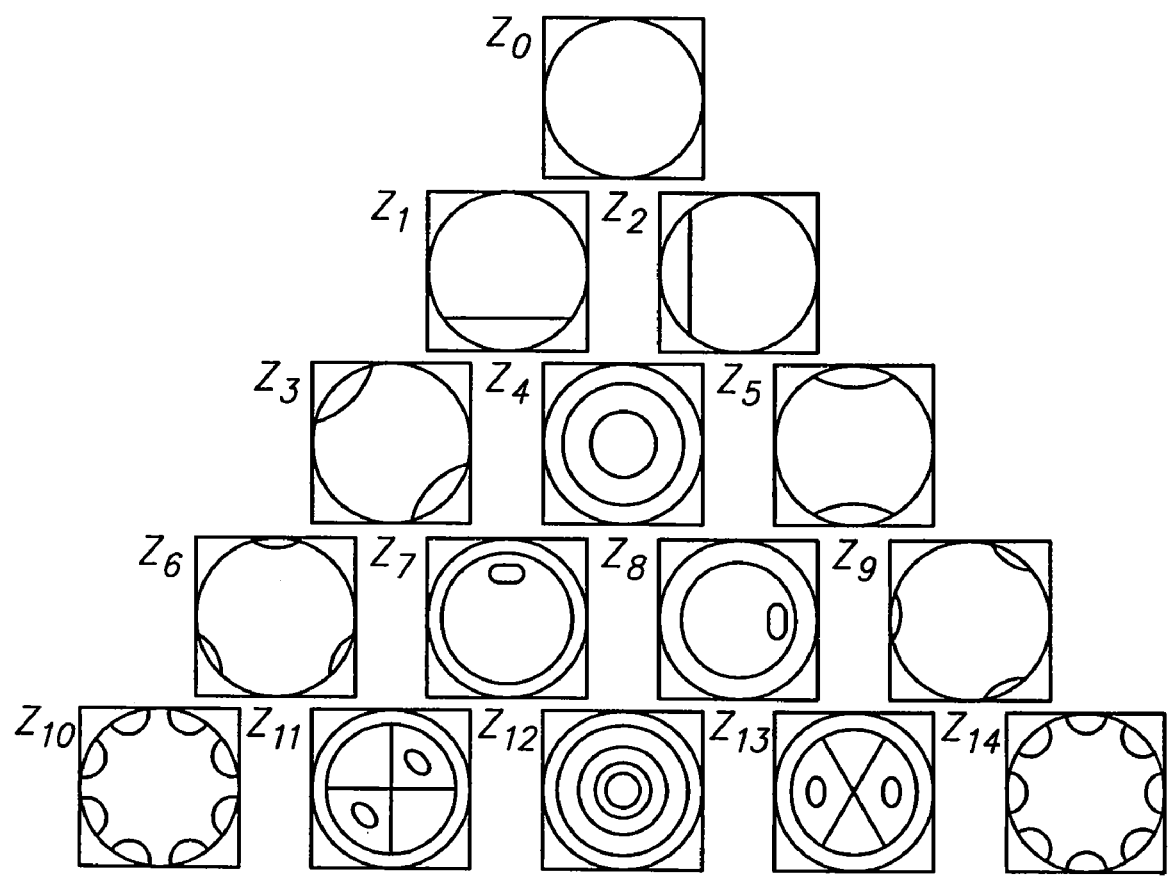
FIG. 4 is a presentation of patterns in accordance with Zernike polynomials for use with the present invention.

Referring now to FIG. 4, patterns are illustrated in accordance with Zernike polynomials for use with the present invention. As stated above, for the present invention, each finite element model in the library will characterize a cornea that exhibits a particular vision defect. Typically, the finite element models utilize Zernike polynomials. More particularly, selected Zernike polynomials can be used with selected corneal configurations. In FIG. 4, certain Zernike polynomials are illustrated. For instance: myopia ($Z_4$); hyperopia ($Z_4$); presbyopia ($Z_4$); astigmatism ($Z_3$ and $Z_5$: $2^{nd}$ order); coma ($Z_7$ and $Z_8$: $3^{rd}$ order); trefoil ($Z_6$ and $Z_9$: $3^{rd}$ order); and spherical aberrations ($Z_{12}$: $4^{th}$ order).

While the particular System and Method for Simulating an LIOB Protocol to Establish a Treatment Plan for a Patient as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for simulating a Laser Induced Optical Breakdown (LIOB) protocol to establish a surgical LIOB treatment for a patient, the system comprising:

a library including a plurality of nomograms and a plurality of finite element models, wherein each nomogram specifies an LIOB treatment protocol for a particular vision defect and wherein each model characterizes a corneal configuration for a particular vision defect, and further wherein each model corresponds to at least one nomogram for the same particular vision defect; and a computer means for conjunctively selecting a nomogram and a corresponding model according to a same particular vision defect, to create an initial corneal configuration, and for selectively individualizing the initial corneal configuration with diagnostic patient data to create an individualized corneal configuration to simulate LIOB thereon in accordance with the LIOB treatment protocol specified by the nomogram using the finite element model selected, and to modify the selectively individualized corneal configuration to establish the surgical LIOB treatment for the particular vision defect.

2. A system as recited in claim 1 wherein each selected nomogram and each corresponding model are associated with a same Zernike polynomial.

3. A system as recited in claim 2 wherein each nomogram is compiled with data collected from a plurality of patients.

4. A system as recited in claim 3 wherein the LIOB treatment protocol specified by each nomogram corrects a respective vision defect selected from a group consisting of myopia, hyperopia, presbyopia, astigmatism, coma and trefoil.

5. A system as recited in claim 3 wherein the plurality of patients includes more than one hundred patients.

6. A system as recited in claim 1 further comprising:
a means for determining the modified corneal configuration resulting from simulated LIOB; and
a means for comparing the modified corneal configuration with a desired corneal configuration to identify an error signal for a subsequent selective minimization of the error signal.

7. A system as recited in claim 6 wherein subsequent selective minimization of the error signal requires revision of the LIOB treatment protocol and LIOB simulation on the modified corneal configuration in accordance with the revised LIOB treatment protocol.

8. A system as recited in claim 1 wherein each finite element model comprises:
a first plurality of elements for simulating biomechanical characteristics for a Bowman's capsule of a cornea; and
a second plurality of elements for simulating biomechanical characteristics for a stroma of the cornea.

9. A computer system for establishing a Laser Induced Optical Breakdown (LIOB) treatment plan for a patient which comprises:
a plurality of nomograms installed on a computer, with each nomogram specifying an LIOB treatment protocol for a particular vision defect;
a plurality of finite element models installed on the computer, with each finite element model characterizing a corneal configuration for a particular vision defect;
a means for selecting a nomogram from the plurality of nomograms
according to a particular vision defect, and for selecting a finite element model from the plurality of finite element models according to the same particular vision defect, with the selected finite element model creating an initial corneal configuration;
a means for selectively inputting diagnostic patient data into the computer to program the selected finite element model to create an individualized corneal configuration; and a means for simulating LIOB in accordance with the LIOB treatment protocol specified by the nomogram using the selected finite element model to establish the treatment plan for the particular vision defect.

10. A computer system as recited in claim 9 further comprising:
- a means for determining a modified corneal configuration resulting from the LIOB treatment protocol specified by the nomogram; and
- a means for comparing the modified corneal configuration with a desired corneal configuration to identify an error signal, and to determine whether a subsequent minimization of the error signal by revising the LIOB treatment protocol is required.

11. A computer system as recited in claim 10 wherein the comparing means determines whether the selected finite element model must be replaced with an additional finite element model.

12. A computer system as recited in claim 9 wherein each finite element model comprises:
- a first plurality of elements for simulating biomechanical characteristics for a Bowman's capsule of a cornea; and
- a second plurality of elements for simulating biomechanical characteristics for a stroma of the cornea.

13. A method for establishing a surgical Laser Induced Optical Breakdown (LIOB) treatment plan for a patient which comprises the steps of:
- installing a plurality of finite element models on a computer;
- selecting a finite element model to characterize a particular vision defect of the patient's cornea with a corneal configuration;
- individualizing the corneal configuration with diagnostic patient data;
- inputting a nomogram into the computer to specify an LIOB treatment protocol, wherein the nomogram is representative of a treatment for the same particular vision defect characterized by the finite element model;
- simulating the LIOB in accordance with the LIOB treatment protocol specified by the nomogram using the selected finite element model to create a modified corneal configuration from the individualized corneal configuration; and
- creating a final treatment plan for the particular vision defect in view of the modified corneal configuration.

14. A method as recited in claim 13 further comprising the steps of creating a library, wherein the library includes the plurality of models and a plurality of nomograms.

15. A method as recited in claim 13 further comprising the steps of:
- comparing the modified corneal configuration with a desired corneal configuration to identify an error signal;
- determining whether a subsequent minimization of the error signal by revising the nomogram is required; and
- evaluating the error signal to determine whether an additional finite element model is required for characterizing the modified corneal configuration.

16. A method as recited in claim 15 wherein each finite element model comprises:
- a first plurality of elements for simulating biomechanical characteristics for a Bowman's capsule of a cornea; and
- a second plurality of elements for simulating biomechanical characteristics for a stroma of the cornea.

17. A method as recited in claim 14 wherein each nomogram is based on data collected from a plurality of patients, wherein each finite element model corresponds to at least one nomogram, and wherein each selected nomogram and each corresponding model are associated with a same Zernike polynomial.

* * * * *